US005408532A

United States Patent [19]

Yokota et al.

[11] Patent Number: 5,408,532

[45] Date of Patent: Apr. 18, 1995

[54] VEHICLE INTERNAL NOISE REDUCTION SYSTEM

[75] Inventors: Keitaro Yokota, Hoya; Manpei Tamamura, Ohta; Eiji Shibata, Gunma; Hiroshi Iitaka, Koganei, all of Japan

[73] Assignee: Fuji Jokogyo Kabushiki Kaisha, Tokyo, Japan

[21] Appl. No.: 154,074

[22] Filed: Nov. 18, 1993

[30] Foreign Application Priority Data

Dec. 25, 1992 [JP] Japan .................................. 4-346885

[51] Int. Cl.6 .............................................. A61F 11/06

[52] U.S. Cl. ........................................ 381/71; 381/94; 181/206

[58] Field of Search ................ 123/339, 478; 181/206; 381/71, 86, 94

[56] References Cited

U.S. PATENT DOCUMENTS

| | | | |
|---|---|---|---|
| 4,025,724 | 5/1977 | Davidson, Jr. et al. | 181/206 |
| 4,506,380 | 3/1985 | Matsui | 381/71 |
| 4,753,318 | 6/1988 | Mizuno et al. | 181/206 |
| 5,337,365 | 8/1994 | Hamabe et al. | 381/71 |
| 5,343,713 | 9/1994 | Okabe et al. | 381/71 |

FOREIGN PATENT DOCUMENTS

| | | | |
|---|---|---|---|
| 2531023 | 2/1984 | France | 181/206 |
| 86833 | 4/1993 | Japan | 181/206 |

*Primary Examiner*—Willis R. Wolfe

*Attorney, Agent, or Firm*—Beveridge, DeGrandi, Weilacher & Young

[57] ABSTRACT

An ignition pulse shaped and demultiplied is used as a primary source and this primary source is converted into a canceling signal after being subjected to the sum of convolution products process with filter coefficients of an adaptive filter. Further the canceling signal is converted into a canceling sound by a speaker and outputted to the passenger compartment to cancel a vibration noise at a noise receiving point. The state of noise reduction is detected as an error signal by a microphone and the error signal is inputted to an exponential averaging circuit where the error signal is exponentially averaged with previous error signals by a trigger signal of the primary source from a trigger signal generating circuit. The error signal, as a result of this averaging, is compressed and then outputted to a LMS operational circuit. In the LMS operational circuit the filter coefficients are updated based on the primary source inputted via a $C_{MNO}$ circuit and the compressed error signal.

15 Claims, 8 Drawing Sheets

720°CA
t (sec)

(dB)
t (sec)

0.5 1.0 1.5 2.0 2.5 3.0 --- 0.5xn
f (Hz)

0.5 1.0 1.5 2.0 2.5 3.0 --- 0.5xn
f (Hz)

VEHICLE INTERNAL NOISE REDUCTION SYSTEM

BACKGROUND OF THE INVENTION

The present invention relates to a noise reduction system for a passenger compartment of an automotive vehicle by positively generating the sound to cancel the vehicle internal noise.

There have been proposed several techniques for reducing the noise sound generated mainly from an engine and transmitted to the passenger compartment by producing canceling sound from a sound source disposed in the passenger compartment. The amplitude of the canceling sound is the same as that of the noise sound, but the canceling sound has a reversed phase to that of noise sound.

As a recent example, Japanese application laid open No. 1991-178845 discloses a vehicle internal noise reduction technique for reducing a noise sound by using a LMS (Least Means Square) algorithm (a theory for obtaining a filter coefficient by approximating it to a means square error in order to simplify a formula to obtain a filter coefficient: noticing that a filter correction formula is a recursive expression) or by employing a MEFX-LMS (Multiple Error Filtered X-LMS) algorithm (a multi-channeled algorithm of the LMS algorithm). This technique has already been put to practical use in some of vehicles. In an internal noise reduction system using this LMS algorithm, when an internal noise whose primary source is an engine vibration is reduced, a vibration noise source (hereinafter referred to as a primary source, too) is obtained from a signal having a high correlation with an engine vibration. The canceling sound is produced from a speaker after the primary source is synthesized by an optimum filter. Then a reduced sound is detected by a microphone as an error signal. A filter coefficient of the optimum filter is updated by the LMS algorithm based on this error signal and the above primary source so as to optimize the reduced sound at a sound receiving point.

In this prior art technology, however, since in the noise reduction system using the LMS algorithm or the MEFX-LMS algorithm abovementioned the error signal detected by the microphone contains other noise components (random noise signals) than those to be reduced, the filter coefficients are updated being affected by these random signals. As a result of this, the calculation amount in converging the filter coefficients is increased, so that not only a response characteristic becomes poor because the noise control efficiency get worsened, but also an obtainable amount of noise reduction can not be secured because the noise reduction control becomes unstable due to the effects of those random noise signals.

In view of the foregoing, it is an object of the present invention to provide a vehicle internal noise reduction system which has an excellent response characteristic and a good noise reduction performance.

To achieve the abovementioned object, the vehicle internal noise reduction system according to the present invention comprises: input signal transforming means responsive to an ignition pulse signal for transforming the ignition pulse signal into a single vibration noise source signal (primary source) so as to obtain a frequency spectrum composed of $0.5\times n$ order components; canceling signal synthesizing means responsive to the vibration noise source signal for synthesizing the transformed vibration noise source signal into a canceling signal based on filter coefficients of an adaptive filter and for outputting the synthesized canceling signal; canceling sound generating means responsive to the synthesized canceling signal for generating a canceling sound to cancel a vibration noise in a passenger compartment of a vehicle; error signal detecting means for detecting a reduced sound as an error signal at a noise receiving point; noise components compressing means responsive to the vibration noise source signal for compressing the error signal so as to reduce an influence of random noise components other than noises to be reduced contained in the error signal; and coefficients updating means responsive to the vibration noise source signal and the compressed error signal for updating the filter coefficients of the adaptive filter.

Next, based on the composition of means abovementioned, it will be briefly explained how the noise reduction system according to the present invention functions.

First, when a vibration noise originated from an engine is transmitted to the passenger compartment, the vibration noise source signal is synthesized into a canceling signal by the adaptive filter. Then, this canceling signal is transformed into a canceling sound by the canceling sound generating means and the canceling sound is generated from a sound source to cancel the vibration noise. Further, a reduced sound is detected by the error signal detecting means as an error signal. Next, noise components containing in the above error signal are compressed up to a specified level by the noise components compressing means based on the above vibration noise source signal. Finally, based on the vibration noise source signal and the compressed noise components, filter coefficients of the adaptive filter are updated by the coefficients updating means.

Thus, since the noise components other than those to be reduced are compressed up to a specified level, a converging performance of the adaptive filter is improved, whereby the noise reduction system according to the present invention can attain a good response characteristic and an excellent noise reduction performance.

BRIEF DESCRIPTION OF DRAWINGS

FIG. 1 shows a schematic view of the vehicle internal noise reduction system according to a first embodiment of the present invention;

FIG. 2 is an illustration for explaining an ignition signal conversion circuit;

FIG. 3 is an illustration for explaining a relationship between a vibration noise and a vibration noise source signal. An illustration (a) shows a shaped ignition signal pulse, an illustration (b) shows an engine related vibration noise, an illustration (c) shows a shaped ignition signal pulse of frequency domain and an illustration (d) shows an engine related vibration noise of frequency domain;

FIG. 4 shows a result of simulation in processing an exponential averaging;

FIG. 5 illustrates a result of a vibration noise measurement without processing an exponential averaging;

FIG. 6 illustrates a result of a vibration noise measurement in processing an exponential averaging with $N=2$;

FIG. 7 indicates a result of a vibration noise measurement in processing an exponential averaging with $N=4$;

FIG. 8 indicates a result of a vibration noise measurement in processing an exponential averaging with $N=8$;

FIG. 9 indicates a result of a vibration noise measurement in processing an exponential averaging with $N=16$.

DETAILED DESCRIPTION OF THE PREFERRED EMBODIMENTS

The preferred embodiment of the vehicle internal noise reduction system according to the present invention will be described hereinbelow by referring to the attached drawings.

Figure 1:
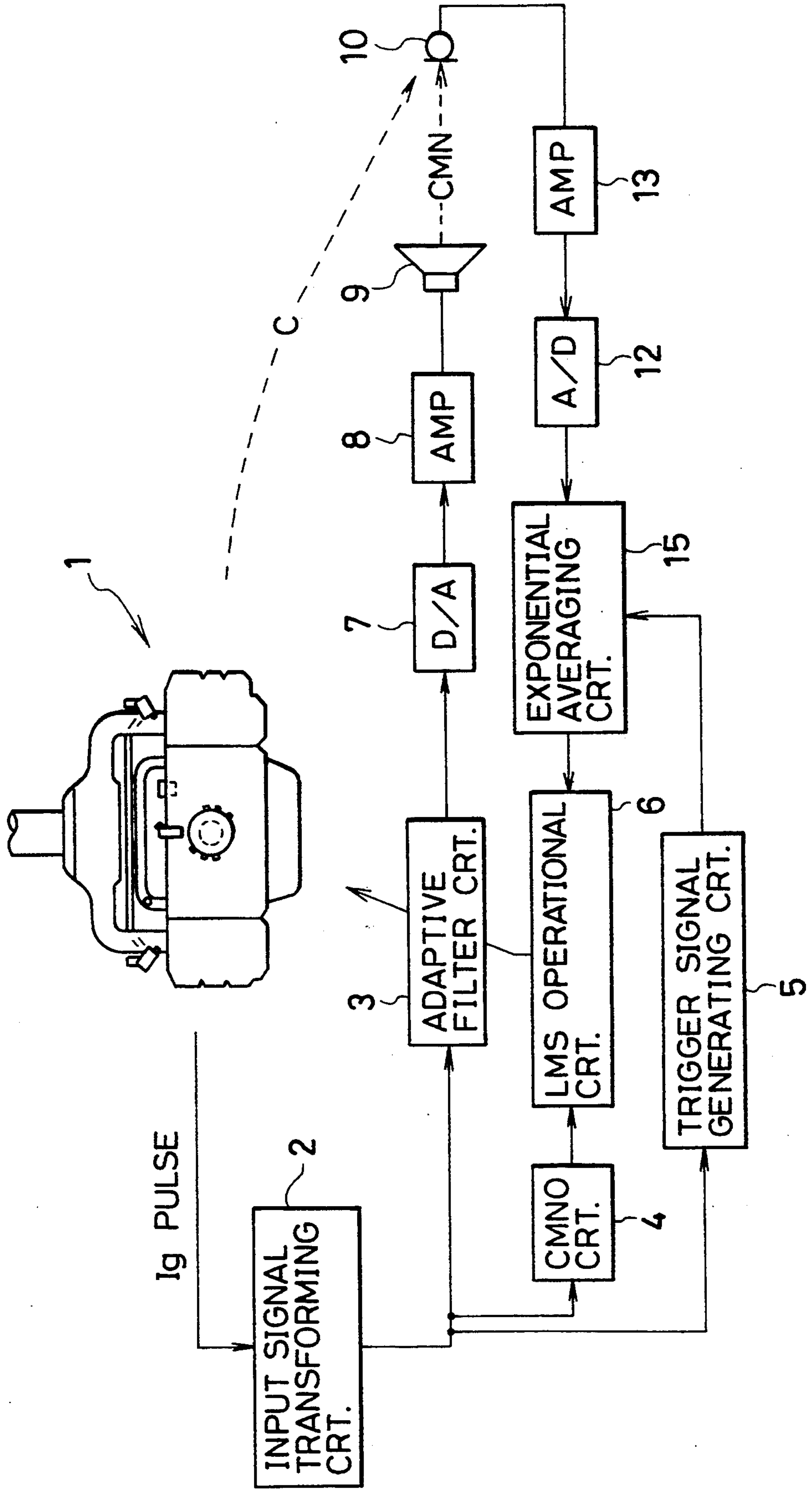
FIG. 1 to FIG. 9 show a first embodiment and FIG. 10 indicates a second embodiment.
Figure 2:
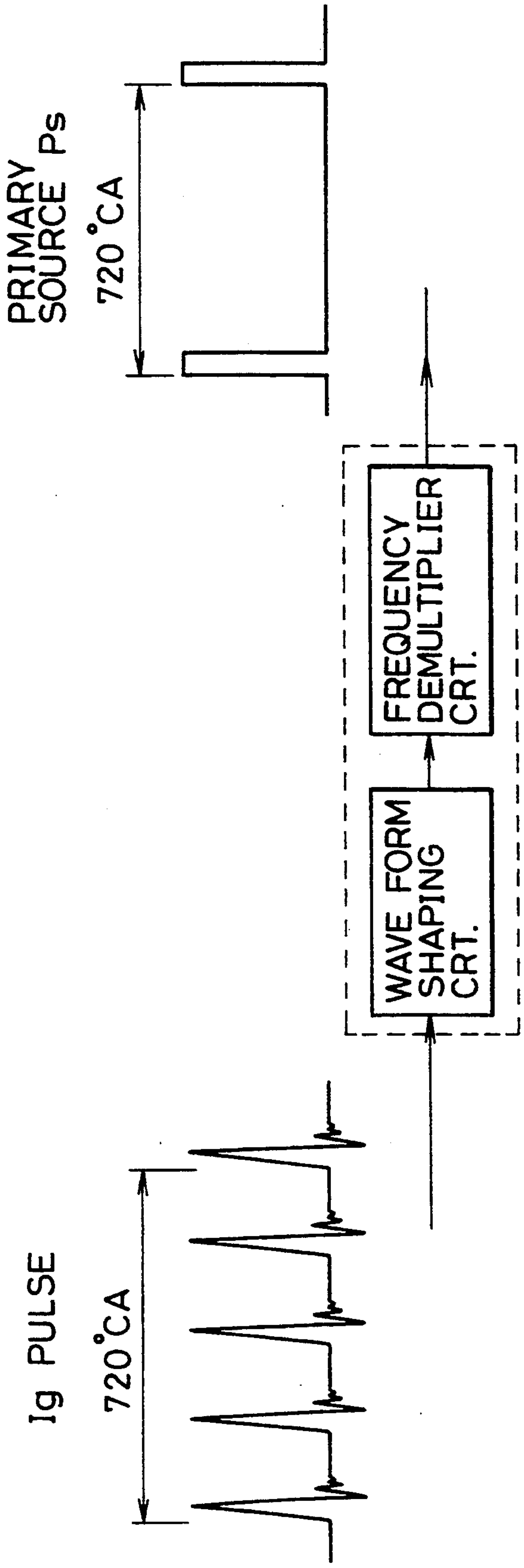
Figures 3A, 3B, 3C, 3D:
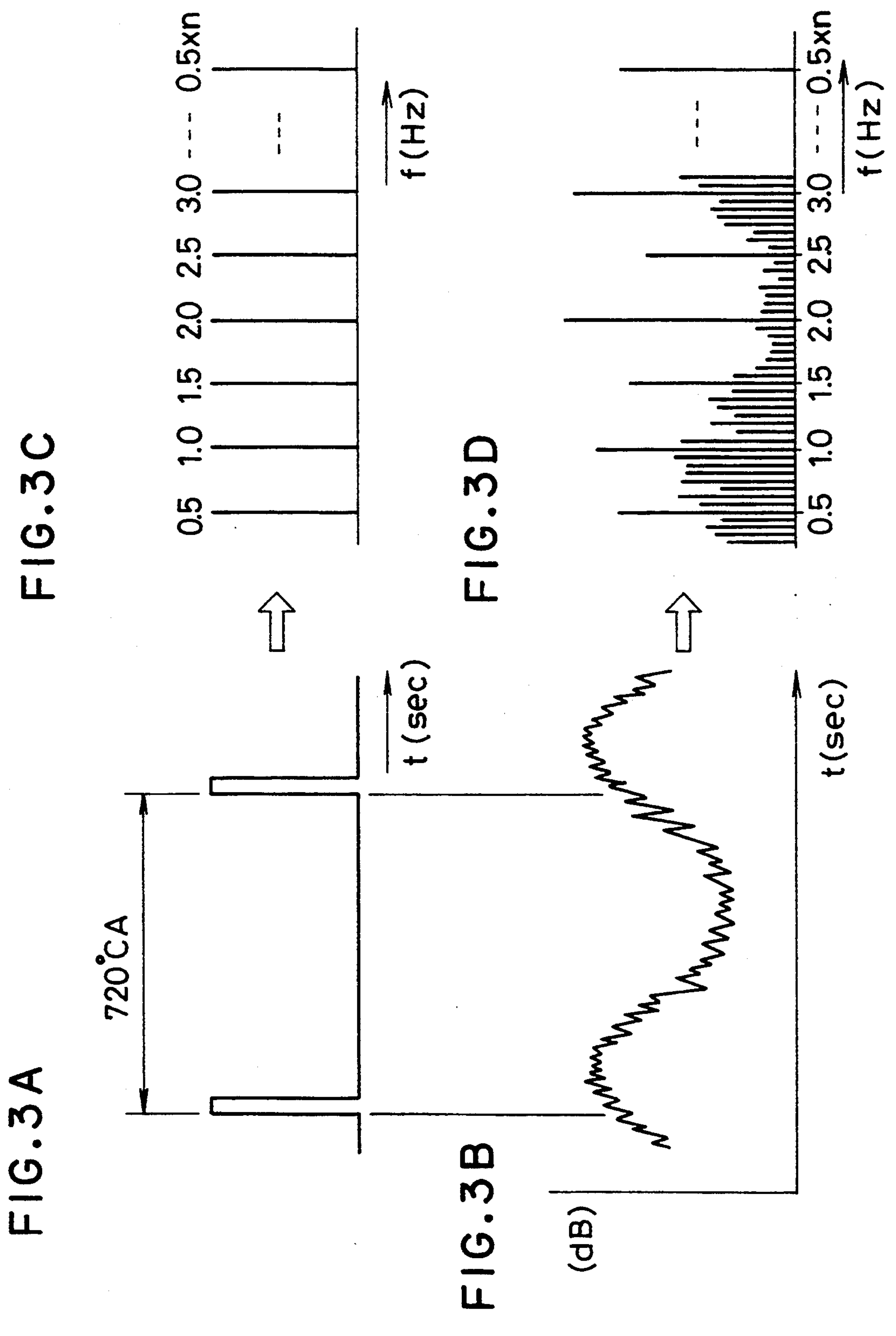

FIG. 1 is a practical block diagram illustrating the first embodiment of the present invention. Reference numeral 1 denotes a four cycle engine whose ignition pulse signal (hereinafter referred to as "Ig pulse signal") is transmitted to an ignition coil (not shown) and at the same time to an input signal transforming circuit 2, too. This input signal transforming circuit 2 is composed of a waveform shaping circuit 2*a* and a frequency demultiplier circuit 2*b*. The Ig pulse signal is synchronized with an engine revolution and forms one cycle per two engine revolutions. The Ig pulse signal from an engine is inputted to the input signal transforming circuit 2 where the Ig pulse signal is shaped and demultiplied into a single pulse signal composed of $0.5\times n$ (n: integers) order components of engine revolution. The pulse signal is outputted as a vibration noise source signal (primary source Ps) to an adaptive filter 3 which is canceling signal synthesizing means, a speaker/microphone transmission characteristic correction circuit (hereinafter referred to as a $C_{MNO}$ circuit) 4 and a trigger signal generating circuit 5 which are noise components compressing means. The vibration noise (FIG. 3 (*b*)) of the four cycle engine is a vibration noise forming one cycle for every two engine revolutions since the engine 1 has four strokes (induction, compression, explosion and exhaust). According to the frequency domain, this vibration noise is expressed as a frequency spectrum mainly composed of $0.5\times n$ (integers) high order components, as shown in FIG. 3 (*d*). Therefore, a primary source Ps having a high correlation with a vibration noise to be reduced can be obtained by shaping and demultiplying the Ig pulse signal as mentioned above. Refer to FIG. 3 (*a*) and FIG. 3 (*c*).

Further, the adaptive filter 3 is a FIR (Finite Impulse Response) filter which has filter coefficients $W_{(n)}$ updated by a LMS operational circuit 6 and has a specified number of taps therein. The LMS operational circuit acts as filter coefficients updating means. The primary source Ps inputted to the adaptive filter 3 is subjected to the convolution sum process with the filter coefficients $W_{(n)}$ and outputted to a D/A converter 7 as a canceling signal. Further the canceling signal is amplified by an amplifier circuit (AMP circuit) 8 via a filter circuit (not shown) and then a canceling sound is generated from a speaker 9 which is canceling sound generating means. The speaker 9 is disposed, for example, at the inner front door (not shown). Further, a microphone 10 which is error signal detecting means is disposed at a noise receiving point (for instance, a position adjacent to a driver' ears) within the passenger compartment. The error signal, namely a reduced sound, which is a result of interference between a canceling sound and an engine related vibration noise, is detected by the microphone 10 and inputted to an exponential averaging circuit 13 which is noise components compressing means via an amplifier circuit (AMP circuit) 11, a filter circuit (not shown) and an A/D converter 12. The exponential averaging described hereinafter in carried out based on a trigger signal generated from the trigger signal generating circuit 5 in response to the primary source Ps. In the exponential averaging circuit 13, the error signal transmitted from the microphone 10 is subjected to the exponential averaging process based on the preceding processed data in response to the trigger signal from the trigger signal generating circuit 5 and then the error signal thus processed are outputted to the LMS operational circuit 6.

On the other hand, in the aforementioned $C_{MNO}$ circuit 4, the speaker/microphone transmission characteristics $C_{MN}$ has been approximated to the infinite impulse response and is stored therein as an approximate value $C_{MNO}$. The inputted primary source Ps is multiplied (sum of convolution products) by the above approximate value $C_{MNO}$ and the primary source Ps thus corrected is outputted to the LMS operational circuit 6. Next, in the LMS operational circuit 6, a corrected amount of the filter coefficients $W_{(n)}$ of the adaptive filter 3 is calculated by the LMS algorithm based on the error signal processed in the exponential averaging circuit 13 and on the primary source Ps corrected by the above $C_{MNO}$ circuit 4 and then the filter coefficients $W_{(n)}$ are updated therein.

Next, the exponential averaging in the exponential averaging circuit 13 will be explained. The formula for the exponential averaging is given as follows.

Where the result of the exponential averaging of this time is $P_{xi}$, the result of the exponential averaging of the last time is $P_{x,i-1}$ and the error signal is $P_i$ of this time;

$$P_{xi}=((N-1)\,P_{x,i-1}+P_i)/N \quad N\text{: parameter } (n>1) \qquad (1)$$

In case of $N=2$ in the above formula, and where the result of the exponential averaging of the second last time is $P_{x,i-2}$, the result of the exponential averaging of the third last time is $P_{x,i-3}$, the error signal of the last time is $P_{i-1}$ and the error signal of the second last time is $P_{i-2}$, the formula (1) is;

$$\begin{aligned}P_{xi} &= ((2-1)P_{x,i-1}+P_i)/2\\ &= (P_{x,i-1}+P_i)/2\\ &= (1/2)P_{x,i-1}+(1/2)P_i\\ &= (1/2)((P_{x,i-2}+P_{i-1})/2)+(1/2)P_i\\ &= (1/2)2P_{x,i-2}+(1/2)2P_{i-1}+(1/2)P_i\\ &= (1/2)2((P_{x,i-3}+P_{i-2})/2)+(1/2)2P_{i-1}+(1/2)P_i\\ &= (1/2)3P_{x,i-3}+(1/2)3P_i-2+(1/2)2P_{i-1}+\\ &\quad (1/2)P_i\end{aligned}$$

From the above expression (2), it is know that the result of $P_{xi}$ of the exponential averaging contains the compressed results of the past error signals and of the past averaging, that is to say, 50% of the this time result $P_i$, 25% of the last time result $P_{i-1}$, 12.5% of the second last time result $P_{i-2}$ and 12.5% of the third last time result $P_{x,i-3}$.

In case of $N=4$ in the formula (1), the formula (1) is;

$$\begin{aligned}P_{xi} &= ((4-1)P_{x,i-1}+P_i)/4 \qquad (3)\\ &= (3P_{x,i-1}+P_i)/4\end{aligned}$$

-continued $$= (3/4)3P_{x,i-3} + (32/43)P_{i-2} + (3/42)P_{i-1} + (1/4)P_i$$

From the above expression (3), it is known that the result $P_{xi}$ contains 25% of the this time result $P_i$, 19% of the last time result $P_{i-1}$, 14% if the second last time result $P_{i-2}$, and 42% of the third last time result $P_{x,i-3}$.

As recognized from above expressions (2) and (3), the greater the parameter N becomes, the smaller the effect of the error signal of this time ($P_i$) to the result of the exponential averaging $P_{xi}$ becomes. In case of N=1, the formula (1) is becomes $P_{xi}=P_i$, that is to say, no exponential averaging is done. It should be noted that the parameter N is not limited to integers.

Figure 4:
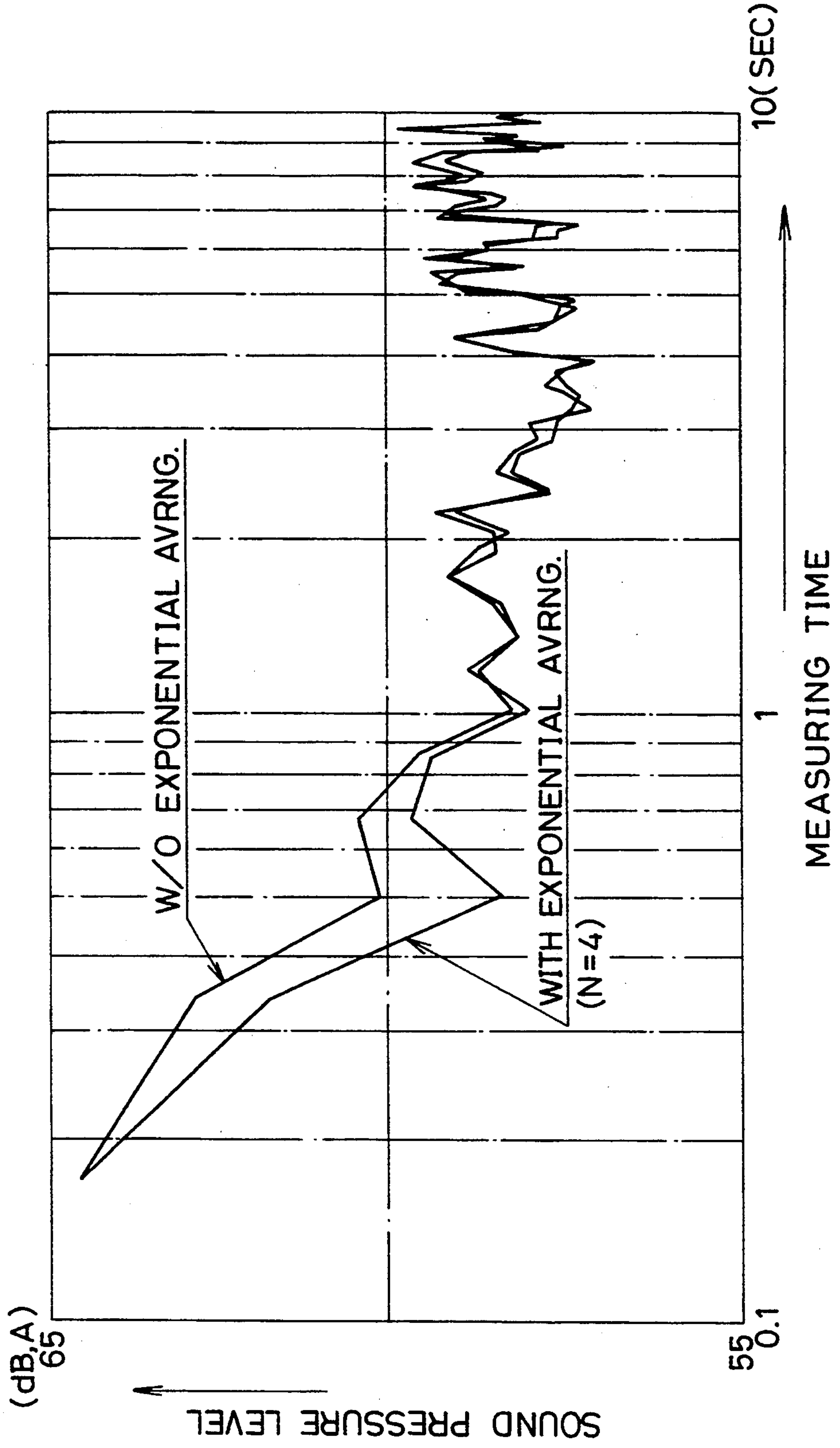
Figure 5:
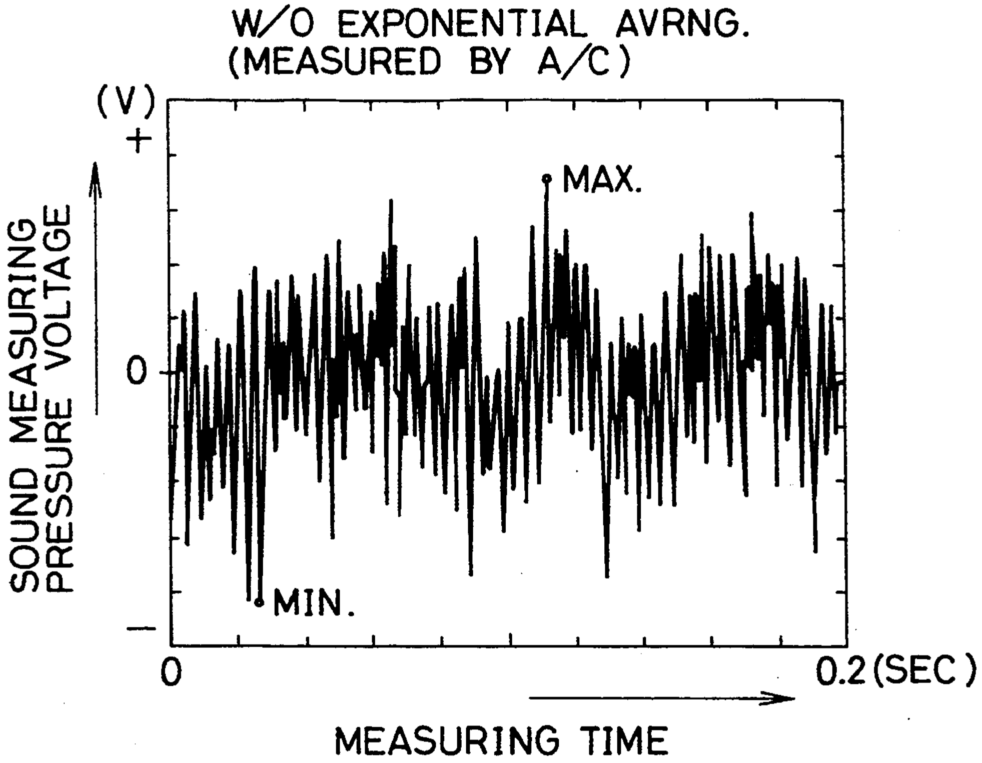
Figure 6:
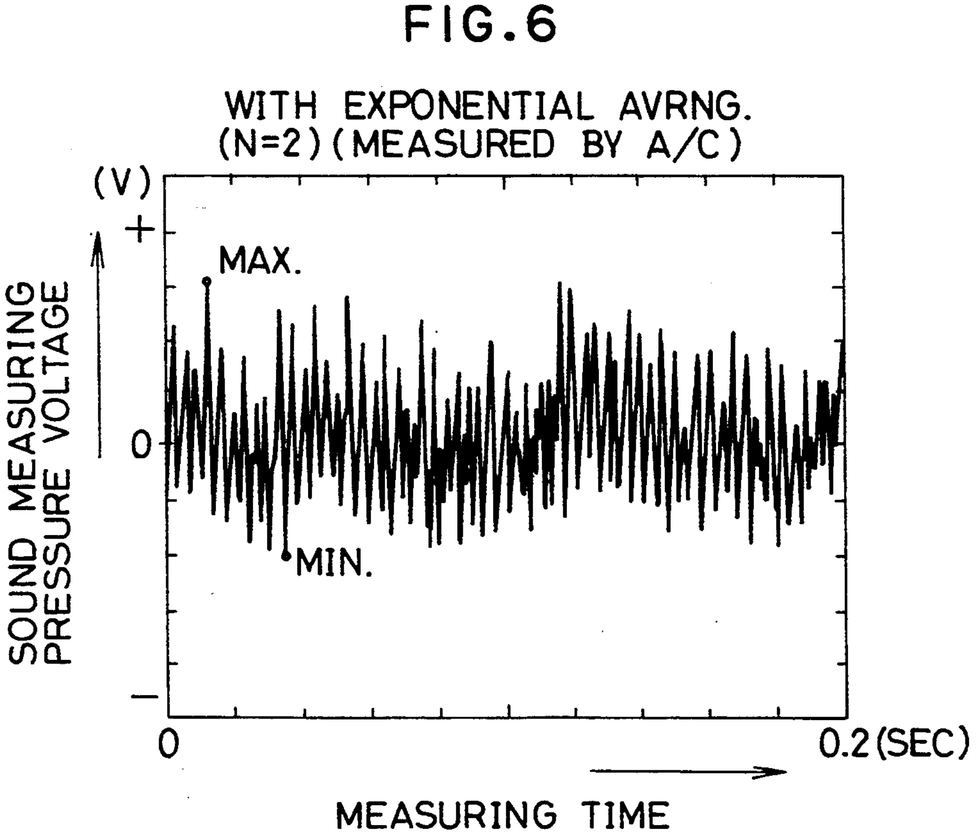
Figure 7:
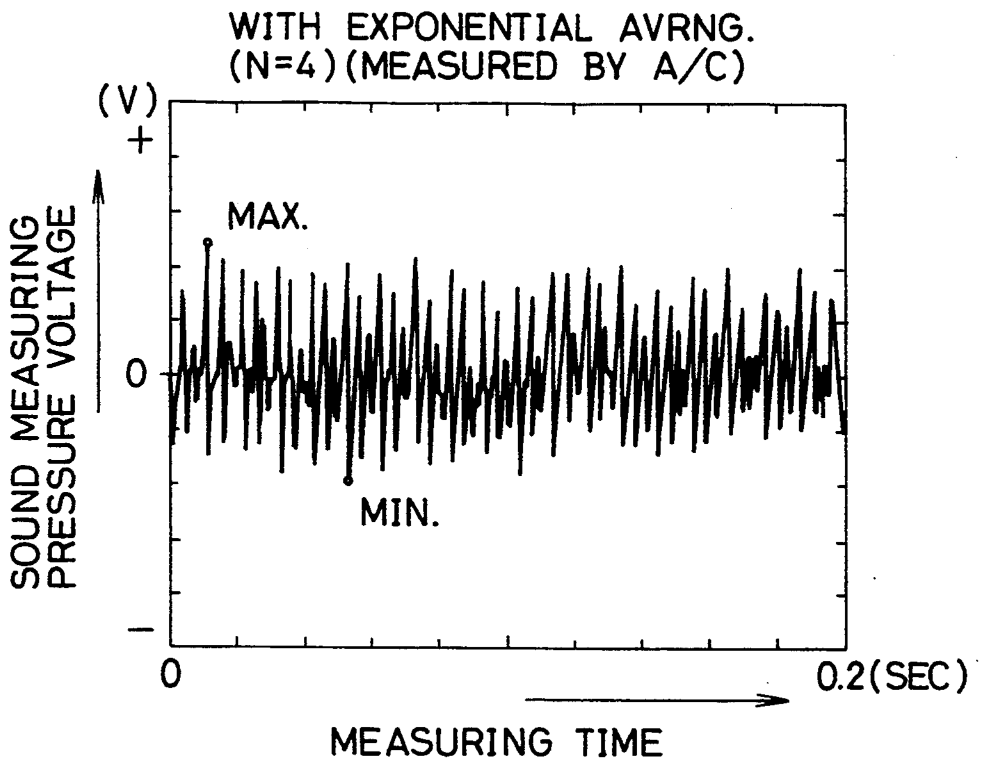
Figure 8:
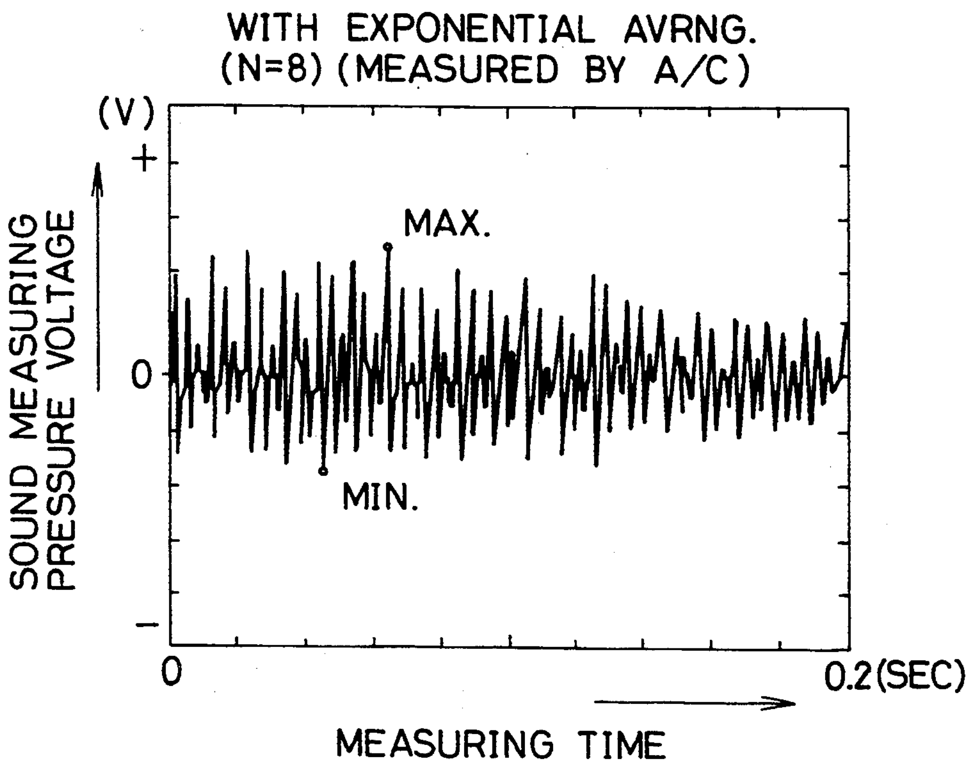
Figure 9:
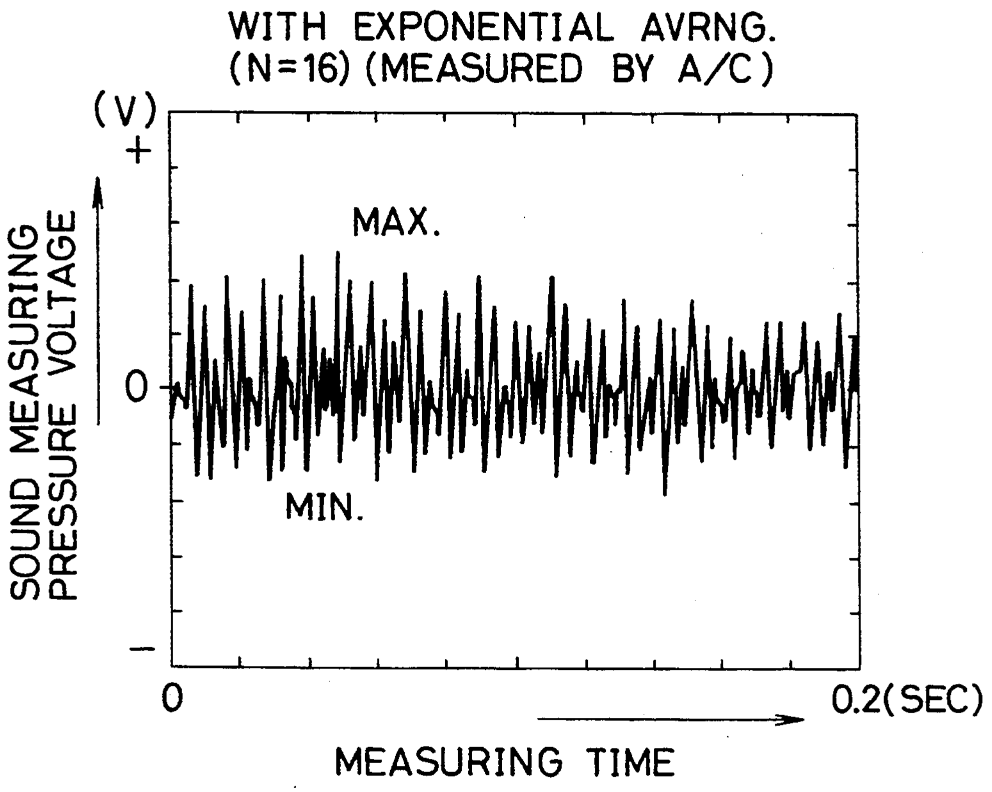

FIG. 5 shows the result of an actual noise measurement when keeping an engine revolution at 6000 rpm. Further, FIG. 6 to FIG. 9 show the results of exponential averagings based on actual noise measurement data when varying the parameter N with keeping an engine revolution at 6000 rpm. Comparing FIG. 5 with FIG. 6 to FIG. 9, it is known that large random peaks, i.e., noise components are eliminated and only small cyclic peaks remain when the exponential averaging is performed. Furthermore, it is known that in case of exponential averaging with N=4 (FIG. 7) the peak level of the sound pressure, when the exponential averaging being performed, is reduced to almost half, compared to the peak level without performing the exponential averaging. It is, further known that the result of exponential averaging at N=8 (FIG. 8) and N=16 (FIG. 9) respectively is almost the same as the result at N=4. Therefore, taking a too large figure N than needed is meaningless and the large number of N, on the contrary, might harm the response characteristics of the system under the transitional operating condition because the portion of the error signal of this time is decreased too much. That is to say, it is necessary that N is chosen to such a way that a stable operation of the system is secured. In this embodiment the exponential averaging circuit 13 is so composed as an error signal is subjected to the exponential averaging process with N=4. FIG. 4 indicates the result of a simulation by computer when the exponential averaging is performed with N=4. The object noise is a vehicle internal noise under a constant speed operating condition with 6000 rpm of engine speed. The frequency band of the noise is 0-500 Hz. From this result, it is confirmed that when the exponential averaging is performed, the noise is converged faster than when the exponential averaging is not performed. A symbol C in FIG. 1 denotes a vehicle body transmission characteristic with respect to a vibration noise of the engine 1.

Next, based on the composition of means abovementioned, in the vehicle internal noise reduction system according to the present invention, it will be explained how the noise reduction system works.

First, the engine vibration noise is transmitted to the passenger compartment through an engine mounting and becomes an internal noise. Further, an induction noise and an exhaust noise are transmitted to the passenger compartment at the same time. These engine related noises are mainly composed of frequency spectrum of 0.5×n (n: integers) order when expressed in the frequency domain, as shown in FIG. 3 (*b*). These noises reach a noise receiving point (for example, a position adjacent to a driver's ears) after being multiplied by a vehicle body transmission characteristic C corresponding to each noise source.

On the other hand, the ignition pulse signal (Ig pulse signal) to the ignition coil (not shown) is inputted to the input signal transforming circuit 2 in which the Ig pulse signal is shaped by the waveform shaping circuit 2*a* and demultiplied by the frequency demultilier circuit 2*b* and is outputted as a vibration noise source signal (primary source Ps) composed of one pulse per two engine revolutions from the input signal transforming circuit 2. The Ig pulse signal is also composed of frequency spectrum of 0.5×n (n: integers) order when expressed in the frequency domain. The Ig pulse, thus shaped and demultiplied, is outputted to the adaptive filter 3, the speaker/-microphone transmission characteristic correction circuit (hereinafter referred to as a $C_{MNO}$ circuit) 4 and the trigger signal generating circuit 5.

The primary source Ps inputted to the adaptive filter 3 is subjected to the sum of convolution process with the filter coefficients $W_{(n)}$ and outputted to the D/A converter 7 as a canceling signal to cancel a vibration noise. Then the canceling signal is outputted to the speaker 9 via a filter (not shown) and the amplifier circuit (AMP circuit) 8 and the canceling sound is outputted from the speaker 9 to cancel the vibration noise at the noise receiving point. It is needless to say that the canceling sound is affected by the speaker/microphone transmission characteristic $C_{MN}$ while the canceling sound is transmitted to the noise receiving point.

At the noise receiving point the engine related vibration noise is interfered with the canceling sound and reduced. The result of the interference of the vibration noise and the canceling sound is detected by the microphone 10 as an error signal. The error signal is inputted to the exponential averaging circuit 13 via the amplifier circuit (AMP circuit) 11, the filter circuit (not shown) and the A/D converter 12. In the exponential averaging circuit 13, the error signal is exponentially averaged with some of the preceding error signals by a trigger signal from the trigger signal generating circuit 5 which is energized upon an input of the primary source Ps. As a result of this averaging, the error signal contains the compressed past error signals therein and then is outputted to the LMS operational circuit 6.

On the other hand, the primary source Ps inputted to the $C_{MNO}$ circuit 4 is subjected to the sum of convolution process with an approximate value of the speaker/-microphone transmission characteristic $C_{MN}$, namely, the approximate value $C_{MNO}$ which is approximated by an infinite impulse response and then this sum of convolution products is outputted to the LMS operational circuit 6. Further, in the LMS operational circuit 6, based on the averaged error signal from the exponential averaging circuit 13 and the primary source Ps corrected by the $C_{MNO}$ circuit 4, the corrected amount of the filter coefficients $W_{(n)}$ of the adaptive filter 3 is calculated by means of the LMS algorithm and the filter coefficients $W_{(n)}$ are updated.

Thus, according to the embodiment of the present invention, since the noise components other than ones to be reduced (for example, noise components of a road noise) fluctuate at every cycle, these intermittent, or random noise components are compressed by the exponential averaging process and resultantly the filter coefficients $W_{(n)}$ of the adaptive filter 3 are never updated significantly, even though these random noise signals are contained in the error signal. That is to say, the increase of the amount of calculation for converging the filter coefficients can be prevented and as a result of this, the improved noise control system according to the embodiment of the present invention can attain a system having a high efficiency, an excellent response characteristic, a stable controlability and a good noise reduction performance.

Figure 10:
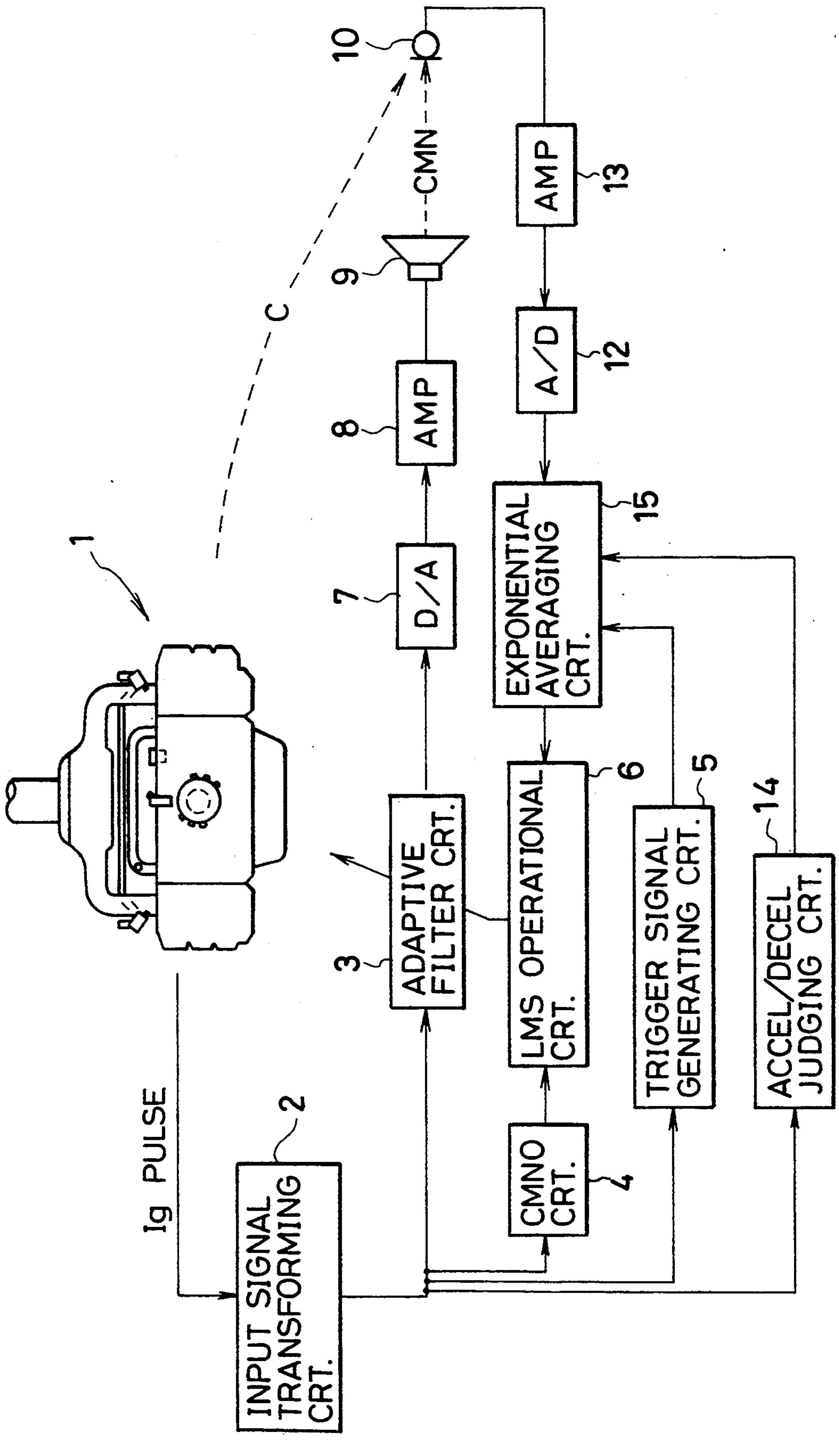
FIG. 10 indicates a schematic view of the vehicle internal noise reduction system according to a second embodiment of the present invention.

Next, according to FIG. 10 the second embodiment of the vehicle internal noise reduction system will be explained. FIG. 10 shows a schematic illustration of the noise reduction system according to the second embodiment. This second embodiment differs from the first embodiment in adding means for being able to vary a parameter N in accordance with the engine acceleration or deceleration in exponentially averaging the error signal. Numerals in FIG. 10 are the same as ones in FIG. 1, so that explanations of numerals will be omitted hereinafter.

Referring to FIG. 10, a numeral 14 denotes an acceleration/deceleration judging circuit. The primary source Ps outputted from the input signal transforming circuit 2 is inputted to the acceleration/deceleration judging circuit 14 in which a degree of acceleration or deceleration of engine revolution is detected. According to the degree of acceleration or deceleration, the parameter N on exponentially averaging the error signal is determined. That is to say, in a transitional operating condition (acceleration or deceleration), the engine related vibration noise is also changed. Under the engine operating condition like this, raising an effect of the error signal provides a prompt updating of the filter coefficients. Based on the primary source Ps inputted to the acceleration/deceleration judging circuit 14, a pulse interval of the last time $Ps_{n-1}$ is compared with a pulse interval of this time $Ps_n$. That is to say, N is given according to the following formula:

$$N=4-\alpha\times|Ps_n-Ps_{n-1}| \quad (4)$$

where; N should be determined within a range of $1\leq N\leq 4$, since N=4 produces a preferable result.
where; $\alpha$ is a constant.

Thus, in the second embodiment of the present invention the exponential averaging of the error signal has been able to be changed according to the degree of acceleration or deceleration of engine revolution, so that the change of the transitional condition can be reflected to the updating process of the filter coefficients promptly and consequently the response characteristic in the transitional condition is improved.

In this embodiment, it is explained that N is calculated according to the formula (4) as described above, however other means for determining N, such as determining N by referring to a map in the memory based on the comparison between the pulse interval of the last time $Ps_{n-1}$ and the pulse interval of this time $Ps_n$, may be available. Further, with respect to the primary source, other engine related primary source Ps having a high correlation with the vibration noise of engine, such as a fuel injection pulse $T_i$, may be used in place of the Ig pulse. Furthermore, in this embodiment, the noise reduction system employs a LMS algorithm of one channel (one microphone and one speaker), however other noise reduction system employing a multi-channel (for example, four microphones and four speakers) algorithm such as a MEFX-LMS (Multiple Error Filtered X-LMS) algorithm may be applied.

In summary, the vehicle internal noise reduction system according to the present invention is characterized in generating the canceling sound synthesized by the adaptive filter to cancel the engine related vibration noise in the passenger compartment, detecting the reduced sound as an error signal, compressing the random noise components other than noises to be reduced in the error signal so as to reduce the influence of these random noise components and updating the filter coefficients based on the compressed error signal. Therefore, since the influence of the random noise components can be reduced, the convergence performance of the filter coefficients is improved, whereby an efficient control for the noise reduction, an excellent response characteristic and a stable and satisfactory noise reduction performance can be obtained.

While the presently preferred embodiment of the present invention has been shown and described, it is to be understood that this disclosure is for the purpose of illustration and that various changes and modifications may be made without departing from the scope of the invention as set forth in the appended claims.

We claim:

1. An internal noise reduction system for an automobile vehicle, the vehicle having, an internal combustion engine mounted on said vehicle, the engine including, an ignition coil for generating at least one ignition pulse signal within one engine cycle, a fuel injector for injecting fuel into a cylinder and an electronic control unit (ECU) for generating at least one fuel injection pulse signal within one engine cycle, the improvement of the system which comprises:

input signal transforming means responsive to said ignition pulse signal for transforming said ignition pulse signal into a single vibration noise source signal (primary source) so as to obtain a frequency spectrum composed of $0.5\times n$ order components;

canceling signal synthesizing means responsive to said vibration noise source signal for synthesizing the transformed vibration noise source signal into a canceling signal based on filter coefficients of an adaptive filter and for outputting the synthesized canceling signal;

canceling sound generating means responsive to the synthesized canceling signal for generating a canceling sound to cancel a vibration noise in a passenger compartment of said vehicle;

error signal detecting means for detecting a reduced sound as an error signal at an noise receiving point;

noise components compressing means responsive to said vibration noise source signal for compressing said error signal so as to reduce an influence of random noise components other than noises to be reduced contained in said error signal; and coefficients updating means responsive to said vibration noise source signal and the compressed error signal for updating said filter coefficients of said adaptive filter.

2. The internal noise reduction system according to claim 1, wherein said input signal transforming means are means responsive to said fuel injection pulse for transforming said fuel injection pulse into a single vibration noise source signal.

3. The internal noise reduction system according to claim 1, wherein said input signal transforming means is an ignition pulse signal transforming circuit including a waveform shaping circuit for shaping a waveform of said ignition pulse signal and a frequency demultiplier circuit for demultiplying said ignition pulse signal into a single pulse.

4. The internal noise reduction system according to claim 1, wherein said input signal transforming means is a fuel injection pulse signal transforming circuit including a waveform shaping circuit for shaping a waveform of said fuel injection pulse signal and a frequency demultiplier circuit for demultiplying said fuel injection pulse signal into a single pulse.

5. The internal noise reduction system according to claim 1, wherein said coefficients updating means includes a speaker/microphone transmission characteristic correction circuit ($C_{MNO}$ circuit) for multiplying (sum of convolution products) said primary source signal by a stored speaker/microphone transmission characteristic approximated to an infinite impulse response and a least means square (LMS) operational circuit for obtaining a correction amount of filter coefficients of said adaptive filter based on said multiplied primary source signal inputted from said $C_{MNO}$ circuit and based on said error signal outputted from said noise components compressing means and for updating said filter coefficients of said adaptive filter based on said correction amount of filter coefficients.

6. The internal noise reduction system according to claim 1, wherein said canceling signal synthesizing means includes an adaptive filter circuit for synthesizing said primary source inputted from said input signal transforming means into said canceling signal by means of multiplying (sum of convolution products) said primary source by the filter coefficients updated in said coefficients updating means.

7. The internal noise reduction system according to claim 1, wherein said canceling sound generating means is at least one speaker disposed in said passenger compartment.

8. The internal noise reduction system according to claim 1, wherein said error signal detecting means is at least one microphone disposed in said passenger compartment.

9. The internal noise reduction system according to claim 1, wherein said noise components compressing means are an exponential averaging circuit for exponentially averaging said error signal so as to reduce an influence of random noise components contained in said error signal.

10. The internal noise reduction system according to claim 9, wherein said error signal is exponentially averaged with the previous error signals.

11. The internal noise reduction system according to claim 9, wherein a parameter N is equal to 4.

12. The internal noise reduction system according to claim 9, wherein a parameter N is an appropriate number within $1 \leqq N \leqq 4$.

13. The internal noise reduction system according to claim 9, wherein a parameter N is an appropriate number determined by a change rate of an engine speed.

14. The internal noise reduction system according to claim 9, wherein a parameter N is an appropriate number determined from a predetermined map parameterizing a change rate of an engine speed.

15. The internal noise reduction system according to claim 13, wherein said parameter N is a number within $1 \leqq N \leqq 4$.

* * * * *